United States Patent [19]

Tonelli et al.

[11] Patent Number: 4,983,780

[45] Date of Patent: Jan. 8, 1991

[54] BRANCHED PERFLUOROALKYL HALIDES AND PREPARATION

[75] Inventors: Claudio Tonelli, Concorezzo; Vito Tortelli, Milan, both of Italy

[73] Assignee: Ausimont S.r.l., Milan, Italy

[21] Appl. No.: 410,472

[22] Filed: Sep. 19, 1989

[30] Foreign Application Priority Data

Sep. 20, 1988 [IT] Italy ................. 22005 A/88

[51] Int. Cl.$^5$ .................. C07C 17/22; C07C 17/24; C07C 17/33; C07C 19/08
[52] U.S. Cl. .................. 57/137; 570/134; 570/173
[58] Field of Search .................. 570/137, 134

[56] References Cited

U.S. PATENT DOCUMENTS

| | | | |
|---|---|---|---|
| 2,880,248 | 3/1959 | Miller | 570/137 |
| 3,008,966 | 11/1961 | Hauptschein et al. | 570/137 |
| 3,377,390 | 4/1968 | Roudestredt | 570/137 |
| 4,243,770 | 1/1981 | Tatemoto et al. | 570/137 |
| 4,359,371 | 11/1982 | Bohm et al. | 570/134 |
| 4,760,205 | 7/1980 | Probst et al. | 570/137 |

*Primary Examiner*—J. E. Evans
*Attorney, Agent, or Firm*—Morgan & Finnegan

[57] ABSTRACT

The present invention relates to new perfluoroalkyl halides and to their preparation by a process based on the thermodecomposition of perfluorocarbides in the presence of $Cl_2$, $Br_2$ and $I_2$.

6 Claims, No Drawings

BRANCHED PERFLUOROALKYL HALIDES AND PREPARATION

DESCRIPTION OF THE INVENTION

The present invention relates to new branched perfluoroalkyl halides selected from the following classes:

(a) branched perfluoroalkyl halides having a secondary carbon atom which is bound to the halogen atom and having general formula:

where X=I, Cl, Br; $R_1$ and $R_2$, like or different from each other, are straight or branched perfluoroalkyl radicals having 1 to 5 carbon atoms, provided that $R_1$ and $R_2$ cannot both be $CF_3$;

(b) perfluoroalkyl halides having a tertiary carbon atom which is bound to the halogen atom and having formula:

where $R_3$, $R_4$, $R_5$, like or different from one another, are straight or branched perfluoroalkyl groups containing 1 to 5 carbon atoms, provided that $R_3$, $R_4$, $R_5$ cannot all be $-CF_3$, and that if X=I and $R_3=R_4=-CF_3$, then $R_5$ cannot be $-CF_2-CF_3$ or $-CF_2-CF_2-CF_3$.

The following compounds belong to class (a):

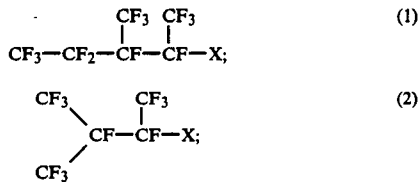

The following compounds belong to class (b):

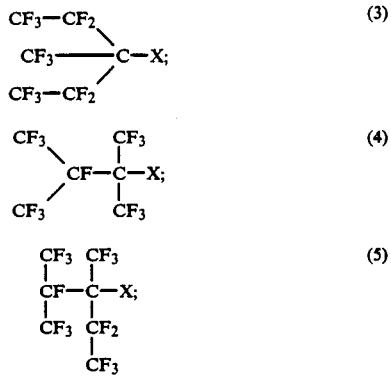

The perfluoroalkyl halides are products of the utmost interest in that they are utilizable in many fields.

The perfluoroalkyl chlorides, for example, can be advantageously utilized as solvents, and cooling liquids. The corresponding bromides and iodides can be utilized as telogens in the radicalic telomerization reaction. The tertiary perfluoroalkyl iodides, owing to the lability of the C-I bond, are utilized in lasers obtained by means of photoiododissociation, where the iodine atom is excited by the action of sunlight (EP 228,701).

The branched perfluoroalkyl halides are not easily synthesized: in the prior art, in fact, the process for preparing them required toxic and expensive reagents such as $IF_5$ or IF. Further, in most of cases, the yields are very low.

For example, J. A. Young and Th. M. Reed in *J. Org. Chem.*, 32 (1967), page 1682, describe the preparation of 2-iodoperfluoro-2-methylpropane, which is the branched perfluoroalkyl halide having the lowest number of carbon atoms, by the reaction of IF with perfluoroisobutylene over 60 hours at 130° C.

H. Fainberg and Braid in *Journal of American Chemical Society* describe the use of a mixture of $IF_5$ and iodine in order to obtain the above said product. Under such conditions, however, it is not possible to obtain long-chain, branched perfluoroalkyl iodides, even if high amounts of catalysts, such as $CoF_3$ and $SbF_5$, are added.

Another method for obtaining 2-iodoperfluoromethylpropane is described by Mochalina, Galacher, and Knuyant in CA66 (1967) 45,901 Y and is based on the reaction of perfluoroisobutylene, in a steel autoclave, with iodine and KF in the presence of a solvent such as nitrobenzene. The reaction is conducted for 10 hours at 180° C. By this method it is possible to obtain high yields of the above said product. However, this process is not capable of providing long-chain branched perfluoroalkyl iodides nor can it be conducted in the absence of solvent.

According to EP 228,701, branched perfluoroalkanes of formula $CF_3(CF_2)_nC(CF_3)_2I$, wherein n=1 or 2, are prepared by reacting the corresponding perfluoroolefins with a mixture of $I_2$ and $IF_5$, in a molar ratio of 2:1 respectively, and at least 1 mole of a metal fluoride selected from LiF, AgF, CuF, KF, RbF, and CsF, at temperatures ranging from 170° C. to 220° C. The perfluoroolefin must be present, in such process, in molar amount five times larger than the molar amount of $IF_5$.

In order to obtain a high yield of the desired product, it is necessary to operate with an excess of metal fluoride with respect to the stoichiometric amount necessary to the reaction.

The metal fluoride excess must be removed from the rough reaction product, which requires, of course, further steps such as washing of the rough reaction product with alkaline water, separation of the organic phase and subsequent anhydrifying before effecting a fractionated distillation of the rough reaction product.

Thus, there is the necessity for a process capable of producing branched perfluoroalkyl halides without the disadvantages of the prior art.

It is known that in perfluoroalkane structures, the strength of the C—C bond decreases as the substitution of the fluorine atoms by perfluoroalkyl groups increases.

PCT published patent application 8007 (in the name of the Ausimont) describes branched perfluoroalkanes having at least a quaternary carbon atom and a tertiary carbon atom, or two adjacent quaternary carbon atoms.

The above said compounds, although stable at room temperature, give rise, by thermal reaction, to decomposition products deriving from the homolytic scission of the C—C bond between the tertiary carbon atom and the quaternary carbon atom or between the two quaternary carbon atoms.

It has now suprisingly been found that it is possible to obtain, with a quantitative yield, branched perfluoroalkyl halides, characterized by a tertiary and/or secondary carbon atom bound to the halide, through thermal decomposition at temperatures ranging from 90° C. to 250° C., preferably from 130° C. to 180° C., in the presence of a halogen of formula $X_2$, wherein $X=Br$, Cl, or I, of branched perfluoroalkanes containing at least 1 tertiary carbon atom and a quaternary carbon atom or 2 adjacent quaternary carbon atoms.

This result is quite unexpected as it was not foreseeable that the formation rate of the perfluoroalkyl halides should be so high and that the reaction should be so selective towards the perfluoroalkyl halides of the invention.

A confirmation of what has been found is obtained by comparing, for example, the kinetic constant relating to the decomposition of the starting perfluoroalkane

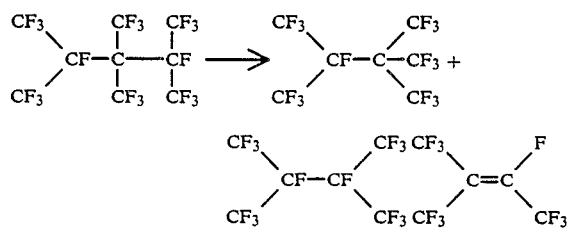

$(1.2 \times 10^{-5}$ at 150° C.; $4.3 \times 10^{-5}$ at 160° C.) with the kinetic constant of the formation reaction, starting from the same substrate, of the perfluoroalkyl halide of formula:

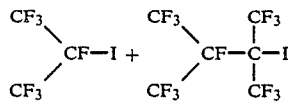

$(2.3 \times 10^{-5}$ at 150° C. and $7.4 \times 10^{-5}$ at 160° C.).

Clearly, the formation rate of the products according to the present invention is equal to about twice the decomposition rate in the absence of halogens.

The process according to the present invention not only produces the new branched perfluoroalkyl halides described in class (a) and class (b) above, but also provides a valid alternative process to produce known products prepared by the above-cited processes of the art, such as for example:

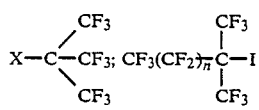

wherein n is 1 or 2, etc.

The perfluoroalkanes utilized as starting materials can be selected for example from:

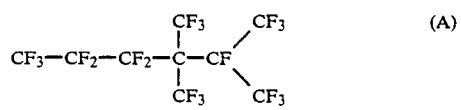

(Chemical Abstract Vol. 101, 121530); in this case, the perfluoroalkyl halides obtained from perfluoroalkane (A) according to the process of the invention are the following:

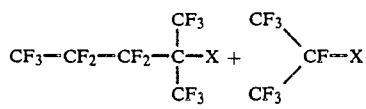

when $X=I$, the product having the highest number of carbon atoms is the product obtained according to EP 228,701, while the other product, in the case that $X=I$, or Br, is known (see EP 142,041).

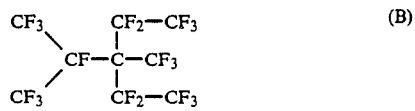

obtained according to U.S. Pat. No. 3,962,358. In this case, the products obtained according to the process of the invention from perfluoroalkane (B) are:

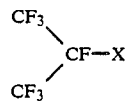

and the product of formula (3) belonging to class (b).

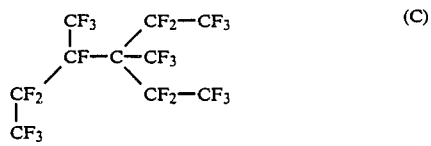

obtained according to U.S. Pat. No. 3,950,235. The products obtained according to the process of the invention from perfluoroalkane (C) are the following:

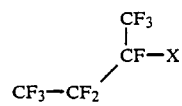

and the above-cited product (3)

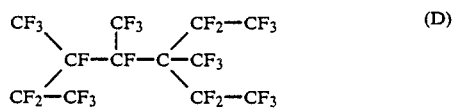

obtained according to U.S. Pat. No. 3,950,235. The corresponding perfluoroalkyl halides obtained from perfluoroalkane (D) according to the process of the invention are the products of formula (1) belonging to class (a) and already cited product (3).

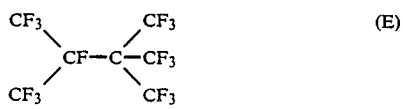

The products obtained according to the process of the present invention from perfluoroalkanes (E) are the following:

$$CF_3-\underset{\underset{CF_3}{|}}{\overset{\overset{CF_3}{|}}{C}}-X \text{ and } \underset{\underset{CF_3}{|}}{\overset{\overset{CF_3}{|}}{C}FX}$$

$$\underset{\underset{CF_3}{|}\ \underset{CF_3}{|}\ \underset{CF_3}{|}}{\overset{\overset{CF_3}{|}\ \overset{CF_3}{|}\ \overset{CF_3}{|}}{CF-C-CF}} \quad (F)$$

prepared according to the PCT published patent application No. 8007. In this case, the product obtained according to the present invention from this perfluoroalkane are product (4), which belongs to class (b), and the product:

$$\underset{CF_3}{\overset{CF_3}{\diagdown}}CF-X$$

$$\underset{\underset{CF_3}{|}\ \underset{CF_2}{|}\ \underset{CF_3}{|}}{\overset{\overset{CF_3}{|}\ \overset{CF_3}{|}\ \overset{CF_3}{|}}{C-C-CF}} \quad (G)$$
$$\underset{CF_3}{|}$$

obtained according to the PCT published patent application No. 8007. In this case, according to the process of the present invention, from perfluoroalkane (G), product (5) and the product $$\underset{CF_3}{\overset{CF_3}{\diagdown}}CF-I$$

are obtained.

$$CF_3-\underset{\underset{CF_3}{|}}{\overset{\overset{CF_3}{|}}{C}}-\underset{\underset{CF_3}{|}}{\overset{\overset{CF_3}{|}}{CF}}-\underset{\underset{CF_3}{|}}{CF} \quad (H)$$

In this case, the perfluoroalkyl halides obtained from perfluoroalkane (H) are $XC(CF_3)_3$ and product (2), which belong to class (a).

At least a stoichiometric amount of fed $I_2$ must be used.

On conclusion of the reaction, the reaction products are separated from the rough reaction product merely by fractionated distillation, as they are easily separated since they have substantially different boiling points.

The following examples are given merely to illustrate but not to limit the present invention.

EXAMPLE 1

(Comparative Test)

Into a glass 50 ml autoclave, 20 g of perfluoroalkane (F) were charged. The autoclave was heated to 161° C. This temperature was maintained for 10 hours, whereafter it was cooled and a product was discharged which, on N.M.R. analysis and I.R. analysis, proved to be composed of, in addition to the starting products:

$$\underset{CF_3}{\overset{CF_3}{\diagdown}}CF-CF\underset{CF_3}{\diagdown} + CF_3-\underset{\underset{CF_3}{|}}{\overset{\overset{CF_3}{|}}{C}}-CF\underset{CF_3}{\diagdown} +$$

$$\underset{F}{\overset{CF_3}{\diagdown}}C=F\underset{CF_3}{\diagdown}$$

Analogous test conducted at a different temperature, during which samplings were taken at time intervals, allowed the calculation of the kdec as a function of the temperature:

| T °C. | kdec |
|---|---|
| 141 | $2.9 \times 10^{-6}$ |
| 151 | $1.2 \times 10^{-5}$ |
| 161 | $4.3 \times 10^{-5}$ |

EXAMPLE 2

Into the same autoclave as used in the preceding example, 20 g of the branched perfluoroalkane of example 1 (0.041 moles) and 31 g of $I_2$ (0.122 moles) were charged. The autoclave was then heated to 161° C. and this temperature was maintained for 6 hours (with sampling at intervals of time to determine the reaction kinetic constant (k)). At the end it was cooled and the rough product was discharged which, on N.M.R. analysis and G.C. analysis, resulted to be composed only of $$\underset{CF_3}{\overset{CF_3}{\diagdown}}CF-I + (d)CF_3-\underset{\underset{CF_3}{|}}{\overset{\overset{CF_3}{|}}{C}}-I$$

(a) (c) (e) (N.M.R. data ref. CFCl$_3$ δ ppm
a = 76; c = 68; e = 60
b = 147 d = 145-146).

Analogous tests at different temperatures gave the same results and permitted the calculation of the kinetic constant as a function of the temperature:

| T °C. | k |
|---|---|
| 151 | $2.3 \times 10^{-5}$ |
| 161 | $7.4 \times 10^{-5}$ |

EXAMPLE 3

Following the same procedure as the preceding example, 30 g (0.061 moles) of the branched perfluoroalkane used in example 2 and 16 g of $I_2$ (0.063 moles) were charged. At the end, the whole was cooled and the rough reaction product was discharged. On N.M.R. analysis and G.C. analysis, it proved to be composed of the products obtained in example 2.

EXAMPLE 4

Into the same autoclave as used in the preceding example, 15 g of the branched perfluoroalkane used in example 2 (0.031 moles) and 14.8 g of $Br_2$ (0.092 moles) were charged. The autoclave was heated to 161° C. and this temperature was maintained for 9 hours. At the end, a rough product was discharged, which proved to be composed of:

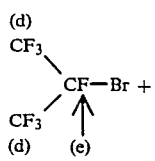

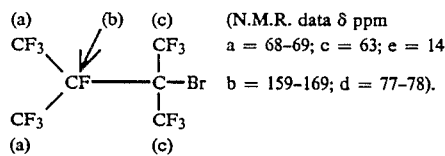

As in example 2, the kinetic constant at different temperatures was calculated:

| T °C. | k |
| --- | --- |
| 141 | $7.0 \times 10^{-6}$ |
| 151 | $2.3 \times 10^{-5}$ |
| 161 | $7.6 \times 10^{-5}$ |

EXAMPLE 5

Into the same reactor as used in the preceding examples 15 g of perfluoroalkane (H) (0.031 moles) and 23.6 g of I$_2$ (0.093 moles) were charged. The charged reactor was heated to 191° C. and was allowed to rest for 8 hours. At the end, a rough product was discharged, which contained about 15% of the staring perfluoroalkane and the following products:

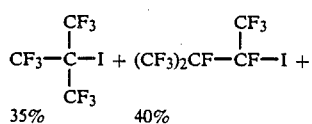

minor amounts (about 10%) of:

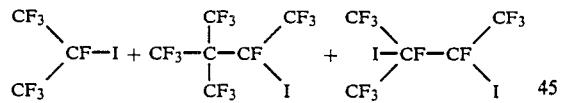

EXAMPLE 6

Into the same autoclave and following the same procedure, 10 g of perfluoroalkane (G) (0.019 moles) and 14.2 g of I$_2$ (0.056 moles) were reacted at 150° C. for 6 hours, then cooled. The rough reaction product was analyzed and proved to be composed of, besides about 10% of unreacted perfluoroalkane:

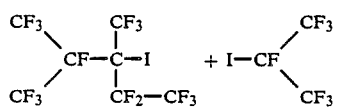

EXAMPLE 7

Into a 50 ml autoclave made of AISI 316 steel, 20 g of perfluoroalkane (F) (0.041 moles), and 8.6 g of Cl$_2$ (0.123 moles) were charged and heated to 150° C. This temperature was maintained for 10 hours. The autoclave was then cooled and the rough reaction product was discharged, which contained the starting perfluoroalkane and:

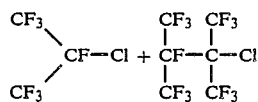

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The reference cited are hereby incorporated by reference.

What is claimed is:

1. Branched perfluoroalkyl halides having a tertiary carbon atom bound to the halogen atom and having the formula:

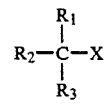

wherein X is I, Cl, or Br; R$_1$, R$_2$, R$_3$, like or different from one another, are straight or branched perfluoroalkyl radicals having 1 to 5 carbon atoms, provided that R$_1$, R$_2$, R$_3$ cannot all be —CF$_3$, and that if R$_1$=R$_2$=—CF$_3$, and X=I, R$_3$ cannot be —CF$_2$—CF$_3$ or —CF$_2$—CF$_2$—CF$_3$.

2. Branched perfluoroalkyl halides according to claim 1, of formula:

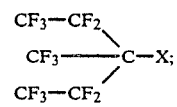

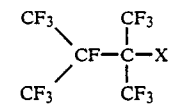

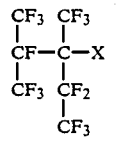

where X is the same as defined in claim 1.

3. Branched perfluoroalkyl halides according to claim 2, of formula:

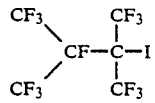

4. Perfluoroalkyl halides according to claim 2, of formula:

5. Perfluoroalkyl halides according to claim 2, of formula:
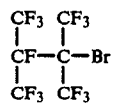
6. Branched perfluoroalkyl halides according to claim 2, of formula:
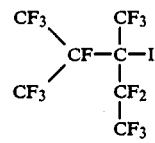
* * * * *